United States Patent [19]

Liboff et al.

[11] Patent Number: 5,183,456
[45] Date of Patent: Feb. 2, 1993

[54] METHOD AND APPARATUS FOR THE TREATMENT OF CANCER

[75] Inventors: Abraham R. Liboff, Birmingham, Mich.; Bruce R. McLeod, Bozeman, Mont.; Stephen D. Smith, Lexington, Ky.

[73] Assignee: Life Resonances, Inc., Bozeman, Mont.

[21] Appl. No.: 902,929

[22] Filed: Jun. 23, 1992

Related U.S. Application Data

[63] Continuation of Ser. No. 703,383, May 21, 1991, which is a continuation of Ser. No. 437,485, Nov. 15, 1989, Pat. No. 5,040,050.

[51] Int. Cl.$^5$ .............................................. A61N 2/00
[52] U.S. Cl. ................................... 600/9; 600/13; 600/15
[58] Field of Search ............... 128/421, 653.1; 600/9, 600/13, 15

[56] References Cited

U.S. PATENT DOCUMENTS

| | | | |
|---|---|---|---|
| 5,045,050 | 9/1991 | Liboff et al. | 600/9 |
| 5,087,438 | 2/1992 | Gordon | 600/9 |
| 5,106,361 | 4/1992 | Liboff et al. | 600/15 |
| 5,108,359 | 4/1992 | Granov et al. | 600/9 |

Primary Examiner—Francis Jaworski
Assistant Examiner—George Manuel
Attorney, Agent, or Firm—Dykema Gossett

[57] ABSTRACT

A method and apparatus for therapeutically treating cancer is provided. The apparatus includes a magnetic field generator for producing a controlled, fluctuating, directionally oriented magnetic field parallel to a predetermined axis projecting through a malignant neoplasm. In one aspect, a field detector measures the magnetic flux density along the predetermined axis. The applied magnetic field may comprise a full-wave rectified signal oscillated at predetermined frequencies to maintain a preselected ratio of frequency to the effective flux density, where the ratio regulates the growth characteristics of cancer cells of the neoplasm. This ratio is maintained by adjusting the frequency of the fluctuating magnetic field and/or by adjusting the intensity of the applied magnetic field after nulling out the local magnetic field at that region containing the neoplasm. In one aspect, a synergistic therapeutic cancer treatment is obtained by exposing cancer cells to the magnetic fields of the invention in the presence of a chemotherapeutic cancer agent.

5 Claims, 3 Drawing Sheets

METHOD AND APPARATUS FOR THE TREATMENT OF CANCER

This is a continuation of copending application Ser. No. 07/703,383 filed on May 21, 1991 which is a continuation application of U.S. patent application Ser. No. 07/437,485 filed on Nov. 15, 1989, now U.S. Pat. No. 5,040,050.

TECHNICAL FIELD

The present invention relates generally to the treatment of cancer. More specifically, it provides in one aspect a method and apparatus by which a reduction in the proliferation rate of cancer cells is achieved through the use of fluctuating magnetic fields which are tuned to preselected frequencies. In the presence of a chemotherapeutic agent, target cancer cells are exposed to the therapeutic fields, producing a reduction in the proliferation of cancer cells greater than that of the chemotherapeutic agent alone. In another aspect, the present invention reduces malignancy by potentiating differentiation of the cells.

BACKGROUND OF THE INVENTION

Approximately one-fifth of all deaths in the United States are caused by cancer. An estimated $20 billion is spent annually in the United States in connection with the care and treatment of cancer patients. Although vast sums are spent on cancer research worldwide, little is known about the initiation and progression of this disease.

As will be appreciated by those skilled in the art, cancer cells are relatively autonomous in that they fail to respond to normal biological signals that control cellular growth and metabolism in the living organism. Malignant tumors are characterized by their ability to metastasize. In metastasis, cancer cells spread through the organism producing tumors at sites remote from the point of origin. It is generally accepted that the number of cell membrane processes is inversely proportional to the probability of cell metastasis. Malignant neoplasms are generally classified as those arising from supportive tissues such as connective tissue, bone, cartilage or striated muscle (sarcomas) and those arising from epithelial tissue (carcinomas). In another type of cancer known as "leukemia," cancer cells circulate predominantly in the bloodstream. In general, leukemias originate in the lymphatic tissues and bone marrow where blood components are formed. After a neoplasm develops in an organism, it may progress from a benign form to a malignant form or from a low-level malignancy to a rapidly proliferating malignancy. Although millions of cells may metastasize from a primary tumor, it is known that only a few of these cells actually result in metastatic lesions at other sites.

While the behavior of cancer cells is unpredictable, it is generally acknowledged that early recognition of cancer is paramount to successful treatment. The most common modern-day method of treating cancer is surgical intervention. Both primary tumors and metastatic tumors may be surgically removed. It is also known that malignant tumors, particularly lymphomas, leukemias and carcinomas can be treated by radiation therapy, for example by exposure to gamma rays and the like. More recently, advances have been made in the use of chemotherapeutic agents, often in conjunction with surgical and/or radiation treatment. It will be appreciated by those skilled in the art that rapidly progressing cancers have a high percentage of cells undergoing mitosis, i.e. a large growth fraction, and it is these cancers that are particularly susceptible to chemotherapy. More recently, immunotherapeutic techniques which utilize antibodies to which cytocidal agents are linked have met with limited success. However, the need for a more effective treatment for cancer is clearly evidenced by the large number of cancer deaths worldwide.

In U.S. Pat. No. 4,622,952, entitled "Cancer Treatment Method," a method of cancer treatment is described by which the application of external electromagnetic energy allegedly achieves biophysical alterations including thermal changes, the stimulation of intracellular interferon production and the stimulation of intracellular prostaglandin production. The process includes the step of empirically tuning external electromagnetic energy to a "resonant" frequency which achieves a precise increment of heat rise within the cancer cell and which stimulates the intracellular production of interferon and/or prostaglandins. The present invention utilizes a group of resonant frequencies, not derived from heating consideration, but derived instead from a basic formula that acts to selectively control the transport of various electrolyte ions into and out of cancer cells, in a manner resulting in substantially no measurable temperature increase within the cells.

In recent years, multi-disciplinary investigations of physiological processes have provided evidence suggesting that electric and magnetic fields play an important role in cell and tissue behavior. In U.S. Pat. No. 4,818,697, entitled "Techniques for Enhancing the Permeability of Ions Through Membranes," which has been assigned to the assignee of the present invention and the disclosure of which is incorporated herein by reference, a method and apparatus are disclosed by which transmembrane movement of a preselected ion is magnetically regulated using a time-varying magnetic field. The fluctuating magnetic field is preferably tuned to the cyclotron resonance energy absorption frequency of the preselected ion. This important discovery brought to light the interplay of local magnetic fields and frequency dependence in ion transport mechanisms.

In U.S. patent application Ser. No. 172,268, filed Mar. 23, 1988, the disclosure of which is incorporated herein by reference, the inventors of the present invention disclose that cyclotron resonance can be used to control tissue development. In U.S. patent application Ser. No. 254,438, entitled "Method and Apparatus for Controlling the Growth of Non-Osseous, Non-Cartilaginous, Solid Connective Tissue," filed Oct. 6, 1988, the disclosure of which is incorporated herein by reference, the present inventors disclose a method of controlling the growth of non-osseous, non-cartilaginous connective tissue which utilizes cyclotron resonance frequencies. In U.S. patent application Ser. No. 295,164, entitled "Techniques for Controlling Osteoporosis Using Non-Invasive Magnetic Fields," filed Jan. 9, 1989, the disclosure of which is incorporated herein by reference, the present inventors disclose a method of controlling osteoporosis using cyclotron resonance magnetic fields. In U.S. patent application Ser. No. 343,017, filed Apr. 25, 1989, entitled "Methods and Apparatus for Regulating Transmembrane Ion Movement Utilizing Selective Harmonic Frequencies and Simultaneous Multiple Ion Regulation," the disclosure of which is incorporated herein by reference, the present inventors disclose a method of utilizing therapeutic higher-harmonic frequencies and a method of simultaneously controlling the transport of multiple ions. In U.S. patent application Ser. No. 395,247, filed Aug. 17, 1989, entitled "Treatment for Stroke Victims," the present inventors describe a method and apparatus for magnetically treating stroke victims.

The present invention discloses a new and unique apparatus for non-invasive treatment of cancer which is directed at reducing the rate of growth of neoplasms through the action of a fluctuating magnetic field.

SUMMARY OF THE INVENTION

In one aspect, the present invention provides an apparatus for decreasing the proliferation rate of cancer cells in the presence of a chemotherapeutic agent. That is, the conventional reduction in the number of cancer cells produced by exposing the cells to a chemotherapeutic agent is enhanced by the magnetic fields of the present invention. The inventive apparatus includes means for generating an applied magnetic flux parallel to a predetermined axis and projecting through a predetermined space. The predetermined space is occupied by cancer cells or a tumor present in a living subject, preferably either man or animal, in the presence of a chemotherapeutic agent. It should also be noted that the present invention may also be useful in the treatment of plant tumors. Means for measuring total magnetic flux density parallel to the predetermined axis extending through the predetermined space is provided so that the magnetic flux density along the axis can be monitored. Means in association with the flux generating means is provided so that the applied magnetic flux can be oscillated. Finally, means for creating and maintaining a relationship between the rate of fluctuation of the magnetic flux and the intensity of the magnetic flux density is provided, where the predetermined relationship decreases the proliferation rate of the target cancer cells. In another aspect, this predetermined relationship is such that the number of cell membrane processes is increased to decrease metastatic potential.

In one embodiment, the means for applying a magnetic flux includes two opposed field coils arranged in Helmholtz configuration such that an applied magnetic field having known parameters along the predetermined axis can be generated between the coils. In another embodiment, a second pair of field coils are placed such that they generate an applied magnetic flux along an axis perpendicular to the predetermined axis defined by the first coil pair. In this same manner, a third pair of opposed coils can be utilized such that magnetic fields are applied by the three coil pairs along the x, y, z axes of a Cartesian coordinate system. The second and third coil pairs are similarly actuated to provide a predetermined relationship between the frequency of the magnetic flux and the intensity of the magnetic flux density.

In another aspect, a method for decreasing the proliferation of cancer cells is provided utilizing the apparatus of the present invention. Therein, a tumor comprising cancer cells in the presence of a chemotherapeutic agent in a living subject, either man or animal, is positioned adjacent to the magnetic field generating means. A specific magnetic flux extending through the space in which the target cancer cells are positioned is generated parallel to a predetermined axis projecting through the cells. A relationship is then created between the frequency of the oscillating magnetic flux and the intensity of the magnetic flux density where the relationship decreases the proliferation rate of the target cancer cells, i.e. the number of cancer cells existing after a predetermined period is less than that with chemotherapy alone. In a preferred embodiment of the present invention, the magnetic flux generating means comprises a pair of field coils as previously described. Also, in a preferred embodiment of the invention, the predetermined therapeutic relationship between the frequency of the magnetic flux permeating the cancer cells and the intensity of the magnetic flux is determined by the cyclotron resonance equation $f_c/B = q/(2\pi m)$, where $f_c$ is the frequency in Hertz, B is the average value of the magnetic flux density in Tesla parallel to the predetermined axis, $q/m$ has a value of from about $5 \times 10^5$ to about $100 \times 10^6$ Coulombs per kilogram and where B has a value of less than about $1 \times 10^{-2}$ Tesla. In a particularly preferred embodiment, $q/m$ is the charge-to-mass ratio of a preselected ion present in the cancer cells.

In still another aspect, a system for decreasing the proliferation of cancer cells is provided which includes means for generating an applied magnetic flux parallel to a predetermined axis and projecting through a predetermined space where the space is occupied by cancer cells of a living subject in the presence of a chemotherapeutic agent. In this particular configuration, the magnetic flux generating means includes at least two opposed field coils having an axis extending through and parallel to the predetermined axis projecting through the predetermined space. Each of the field coils has at least two windings. One winding is designated an ac winding and the other is designated a dc winding. Means in association with the coils is provided for supplying a direct current to the dc winding and an alternating current to the ac winding. Means for measuring the ambient or local field existing in the predetermined space in the region of the cancer cells is also provided. Means in association with the flux generating means for controlling the direct current to the dc windings is supplied such that the dc windings may be activated to create a magnetic flux which reduces the ambient magnetic flux to substantially zero. A full-wave rectifier circuit and an oscillator are provided in association with the ac windings and the current supply means in order to produce an ac magnetic field component along the predetermined axis in the predetermined space which has a preselected rms value, where the rms value decreases the proliferation of cancer cells. In addition, the system may use a sinusoidal signal to the ac windings, offset by a constant bias current equal to the rms-value utilized when full-wave rectification is used.

The system may further include a second pair of opposed field coils which define an axis extending through the region of the cancer cells which is perpendicular to the predetermined axis defined by the first coil pair. Further, a third coil pair can be provided such that the ambient field along the x, y, z axes of a Cartesian coordinate system is reduced to zero, with an applied field having the therapeutic non-zero average value as provided by the present invention being generated along each of the axes.

With respect to the aforementioned system which includes ac windings and dc windings, there is provided by the present invention a method for decreasing the proliferation of cancer cells which comprises the steps of generating an applied magnetic flux parallel to a predetermined axis which projects through a predetermined space, with the space being occupied by cancer cells in a living subject in the presence of a chemotherapeutic agent. The ambient field along the predetermined axis in the predetermined space is measured using a magnetic field sensor which is capable of measuring both static and time-varying magnetic fields. Utilizing the dc windings and a power supply, a magnetic flux is generated which reduces the ambient field to substantially zero along the axis. The ac windings are then used to generate an ac magnetic field having a component along the predetermined axis which has a non-zero average value that is effective in decreasing the proliferation rate of cancer cells.

In still another aspect, the present invention provides a method for the therapeutic treatment of cancer in which the proliferation rate of cancer cells is reduced by the fluctuating magnetic fields provided by the present invention without the concurrent application of a chemotherapeutic agent.

Still further, treatment in accordance with the present invention is in one embodiment effective in stimulating the differentiation of cell processes, i.e., neutrites to decrease the metastatic potential of the cells.

The aforementioned control of cancer cell growth is also achieved to varying extents in one embodiment of the present invention through the use of higher-harmonic tuning and multiple ion tuning is also provided.

DESCRIPTION OF THE PREFERRED EMBODIMENTS OF THE INVENTION

Figure 1:
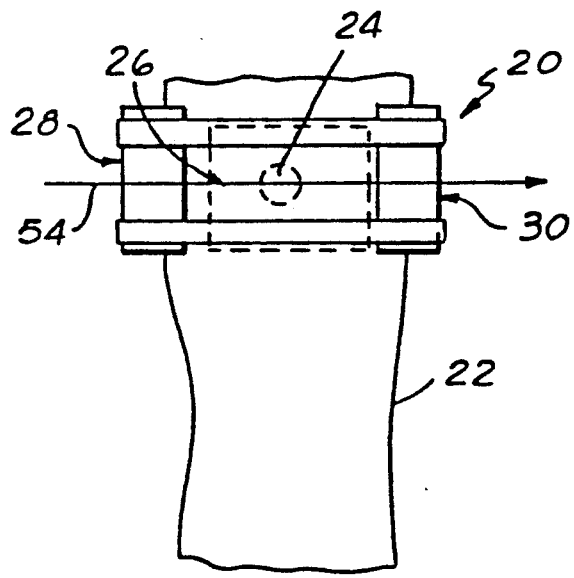
FIG. 1 diagrammatically illustrates one preferred placement of the apparatus of the present invention.

Referring now to FIG. 1 of the drawings, cancer treatment apparatus 20 is shown in position on a subject's leg 22. It is to be understood that both the apparatus and the method of the present invention are suitable for use in decreasing the proliferation rate of cancer cells in both animal and human subjects. As used herein, the term "cancer" shall have its customary meaning, although it is to be noted that the present invention may be useful in the treatment of non-cancerous neoplasms as well as cancerous neoplasms. The term "decreasing the proliferation" and "decreasing the proliferation rate" shall mean that the number of cancer cells existing after a predetermined period of treatment in accordance with the present invention is less per unit volume than the number of cancer cells in a control without treatment in accordance with the present invention. The term "chemotherapeutic agent" shall mean one or more of the various anti-cancer treatment drugs, the identity and nature of which will be known by those of skill in the art. It is known that many of these agents produce a decrease in cancer cell proliferation rates. Thus, the target tissue which is to be affected is a region of cancer cells such as a malignant tumor. Although the present invention has been shown to be useful in decreasing the proliferation rate of neuroblastoma tumor cells in the presence of a chemotherapeutic agent, it is believed that the present invention will be effective in the treatment of other cancer cells, including carcinoma, leukemia, sarcoma, lymphoma, melanoma, myeloma and the like.

A malignant neoplasm 24, shown here as a sarcoma in the subject's thigh, is positioned in a predetermined volume 26 between treatment heads 28 and 30 of cancer treatment apparatus 20. It is within this predetermined space or volume that the therapeutic oscillating magnetic field is generated. Hence, as will be appreciated, there exist within space 26 cancer cells which are multiplying by mitotic division in the uncontrolled manner characteristic of cancers. As with all cancer treatments, it is preferred that treatment by commenced immediately following detection of the condition. In this embodiment of the invention, a chemotherapeutic agent, for example cytosine arabinoside, is administered to the subject in the customary manner. The dosage will be consistent with the known effective dosage for the particular chemotherapeutic agent, although it is anticipated that a reduction in the standard dosage may be facilitated by the present invention. Accordingly, a cancer chemotherapeutic agent is administered to the patient either systematically or locally, for example through the use of cancer cell-specific antibodies to which chemotherapeutic agents are conjugated. The most preferred chemotherapeutic agents which are suitable in the practice of the present invention are those which demonstrate substantially enhanced therapeutic action in the treatment of cancer when administered in connection with selected frequencies of cyclotron resonance tuning as provided by the present invention over control applications of the chemotherapeutic agent without exposure to the magnetic fields of the present invention. This can be readily determined by in vitro or in vivo animal experiments. Preferred chemotherapeutic agents believed to be useful in this respect include alkylating agents and nucleic acid analogs.

Figure 2:
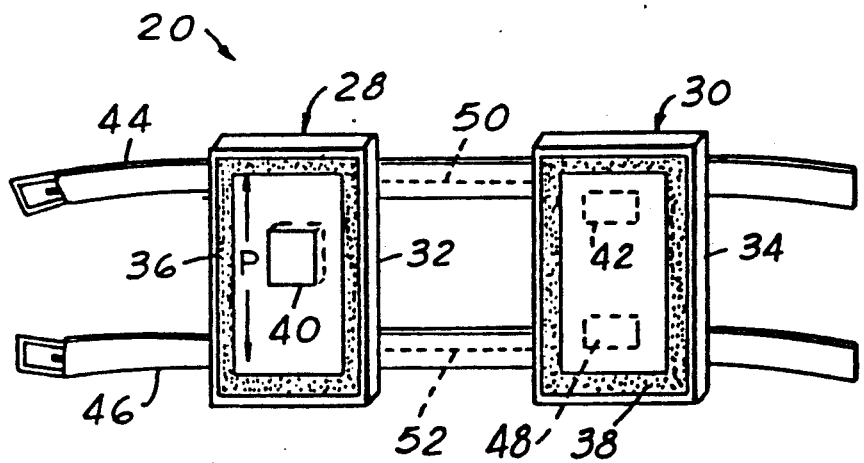
FIG. 2 is a front elevational view of the treatment heads of the present invention in one embodiment.

In order to better appreciate the configuration of treatment heads 28 and 30 as provided by the present invention, reference is now made to FIG. 2 of the drawings in which treatment heads 28 and 30 are shown as including housings 32 and 34 of a non-magnetic material such as plastic. Each housing 32, 34 encloses a field coil 36 and 38. At least one of the treatment heads encloses a magnetic field sensing device 40, such as a Hall-effect device, shown in FIG. 2 enclosed within housing 32 of treatment head 28. The power source for driving the field coils is preferably external, but may be a battery or the like shown as power source 42 in treatment head 30. Straps 44 and 46 are provided by which cancer treatment apparatus can be conveniently attached to the patient.

While field coils 38 and 38 are the preferred means by which an applied magnetic field is generated in the present invention, those skilled in the art will appreciate that other electromagnets or possibly permanent magnets may be adapted for use in the present invention, and any such use is intended to come within the scope of the present invention. Also, the radius of each field coil 36 and 38, as well as the turns of the windings, may vary in accordance with the principles of the present invention. In the most preferred arrangement, the geometry and relative position of treatment heads 28 and 30 during treatment are such that field coils 36 and 38 operate as Helmholtz coils. Hence, those skilled in the art will recognize that in the most preferred arrangement, field coils 36 and 38 are substantially identical, field-aiding, parallel coaxial coils separated by a distance equal to the radius of each coil.

It will be appreciated that the malignant neoplasm to be affected will generally be subject to local magnetic influences. As used herein, the term "local magnetic field," "ambient magnetic field" or the like shall be defined as the magnetic influences, including the earth's magnetic field or geomagnetic field, which create a local magnetic flux that flows through the target tissue. "Magnetic flux density" shall be defined in the customary manner as the number of magnetic field lines per unit area through a section perpendicular to the direction of flux. Factors contributing to the local magnetic field in addition to the geomagnetic field may include localized regions of ferromagnetic materials or the like. In one embodiment of the present invention, field coils 36 and 38 are used to create an applied, fluctuating magnetic field which, when combined with the local magnetic field parallel to a predetermined axis extending longitudinally between treatment heads 28 and 30, produces a combined magnetic field or composite field having a component along the axis which has a precisely controlled, predetermined ratio of frequency to average magnetic flux density.

In one embodiment, and referring again to FIG. 2 of the drawings, this relationship is created using microprocessor 48 which is in communication with electronics necessary to control the oscillation and intensity of the magnetic flux which permeates the target cells. Also, leads 50 and 52 are shown by which the various components of cancer treatment apparatus 20 are interconnected, along with other such leads which are not shown. Magnetic sensor or magnetometer 40 measures the total or composite magnetic flux which passes through the predetermined space between treatment heads 28 and 30 thus providing an accurate measurement of the magnetic field which permeates the malignant neoplasm 24. Predetermined axis 54 is shown in FIG. 1 as extending between treatment heads 28 and 30. It will be appreciated that the applied field generated using treatment heads 28 and 30 may be in either direction of predetermined axis 54 and that the local or ambient magnetic field will also have a component along axis 54 which either augments or decreases the applied magnetic flux. The relatively low applied flux density in the precise, predetermined relationships of combined flux density and frequency provided by the present invention are to be maintained during treatment, notwithstanding the influence of the local magnetic field. This may be achieved in essentially two preferred manners which will be explained more fully herein. Thus, magnetic field sensor 40 is provided to determine the level of the magnetic flux density of the local magnetic field.

Figure 3:
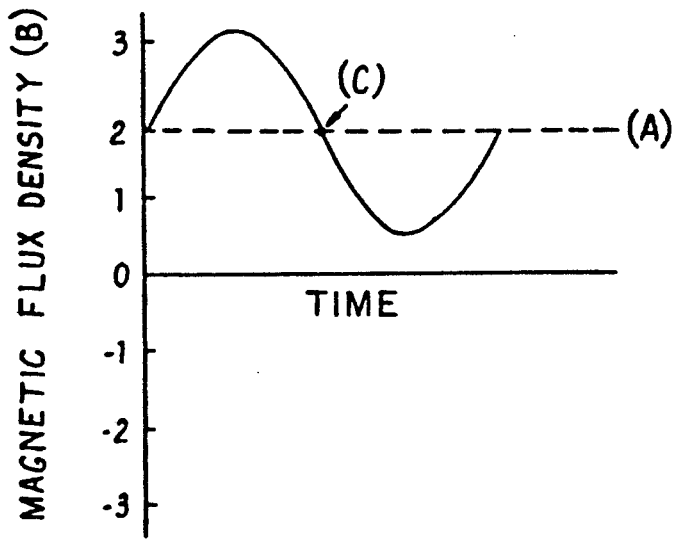
FIG. 3 is a graph which illustrates the magnetic flux density value (B) in the present invention.

The unexpected and superior results of the present invention are achieved by creating a fluctuating magnetic field having a magnetic flux density parallel to predetermined axis 54, with the magnetic flux density along axis 54 being maintained at a predetermined ratio of the frequency of the fluctuations to the non-zero value of the magnetic flux density. In this embodiment, the magnetic flux density parallel to predetermined axis 54 has a non-zero time-average value. More specifically, as illustrated in FIG. 3 of the drawings, the therapeutic magnetic flux of the present invention can be thought of as a static field having reference level A on which a fluctuating magnetic field is superimposed. It comprises a time-varying component which varies in amplitude but not direction and a steady reference value around which the time-varying component varies. Reference level A is the non-zero average value of the flux density (B). Therefore, it will be understood that the non-zero time-average, or net average value where the magnetic field is the combination of the local field and the applied field, along predetermined axis 54 is utilized since the magnitude B of the composite flux density changes at a predetermined rate due to oscillation or fluctuation of the applied magnetic flux. Thus, an average value is utilized which is a non-zero average value illustrated at point (c). This reflects that although the magnetic flux density along the axis is oscillating at a controlled rate, the field is regulated to ensure that the field is always unipolar; that is, the field is always in the same direction along predetermined axis 54.

As stated, it has been found that rather precise relationships of the flux density of the magnetic field to the frequency of the fluctuations are used in the present invention to provide therapeutic results. These ratios of frequency to composite flux density are found in accordance with the following equation:

$$f_c/B = q/(2\pi m)$$

where $f_c$ is the frequency of the combined magnetic field in Hertz, B is the net average value of the magnetic flux density of the magnetic field (the combined field where a local field component is present) parallel to predetermined axis 54 in Tesla and q/m has a value of from about $5 \times 10^5$ to about $100 \times 10^6$ Coulombs per kilograms. B preferably has a value not in excess of about $1 \times 10^{-2}$ Tesla. In order to increase the inhibition of cancer cells in the presence of a chemotherapeutic agent, the following frequency and associated combined magnetic flux density (B) are preferred:

| fc (Hertz) | B (Tesla) |
|---|---|
| 16 | $20.9 \times 10^{-6}$ | at an ac amplitude, peak-to-peak of 40 microTesla.

In use, malignant neoplasm 24 in the presence of a chemotherapeutic agent is then subjected to a fluctuating magnetic field as described herein for a period of time effective to inhibit the rate of growth of the neoplasm by decreasing the proliferation rate of cancer cells. While the length of time necessary for successful treatment may vary, it is anticipated that up to about 100 days of treatment will provide beneficial results. Longer treatment may be desirable in certain applications.

In another embodiment of the present invention, values for q and m are determined with reference to a preselected ionic species. It will be known by those skilled in the art that the biochemical milieu of a malignant neoplasm comprises a mixture of various ions in the intracellular and intercellular fluids. Theses ions include potassium ions, magnesium ions, sodium ions, chloride ions, phosphate ions, sulfate ions, carbonate ions, bicarbonate ions and the like various ions formed by the dissociation of amino acids, proteins, sugars, nucleotides and enzymes. By utilizing the values of charge and mass for a preselected ion in the equation set forth above, which will be recognized by those skilled in the art as the cyclotron resonance relationship solved for $f_c/B$, ratios of frequency to magnetic flux density can be determined which will therapeutically reduce the rate of growth of malignant reoplasm 24 in accordance with the present invention. By using the charge-to-mass ratio of a preselected ion, a specific cyclotron resonance frequency for the ion can be determined. By then tuning cancer treatment apparatus 20 to maintain a combined magnetic flux density having the proper cyclotron resonance frequency, the neoplastic tissue containing the preselected ion can be treated to bring about the desired decrease in the proliferation rate of the cancer cells. More specifically, in a preferred embodiment of the invention, by tuning to $Ca^{++}$ or $K^+$ it is believed that progression of a tumor in the presence of serum lacking fetal growth factors can be slowed in accordance with the present invention.

Hence, it will be appreciated by those skilled in the art that in the present invention, by synergistically enhancing the effects of chemotherapeutic agents in the treatment of cancer, it may be possible to reduce the quantity of or the time course of the chemotherapeutic agents administered to the patient, resulting in a decrease in dose-related effects.

It will also now be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field which has the desired characteristics. However, it is preferred to maintain a constant frequency which thus requires that the intensity of the applied magnetic flux density be adjusted to compensate for changes in the local magnetic field in order to maintain a constant ratio of frequency to magnetic flux density. For example, if it is necessary to maintain a frequency of 16 Hz and an average flux density of $4.07 \times 10^{-5}$ Tela for $K^+$, changes in the local field which would otherwise cause unwanted deviations in the combined magnetic flux density must be corrected by increasing or decreasing the applied magnetic flux density accordingly. This is most preferably performed by the microprocessor in connection with both the field generating means and the field-sensing device. Alternatively, if changes in the combined magnetic flux density occur due to changes in the local magnetic field, the frequency of the oscillations can then be changed so that the preferred ratio is maintained. Once again, it is important to realized that the value of B is the average composite magnetic flux density parallel to the predetermined axis since the magnitude of the flux density changes as the field is oscillated. It will be understood that detection of changes in the magnetic field due to changes in the ambient component should be at intervals frequent enough to provide a frequency-to-magnetic field ratio which is substantially constant, notwithstanding the changes in the local field component.

Referring again to FIGS. 1 and 2 of the drawings, each field coil 36, 38 preferably has up to about 3000 turns or loops of conducting wire, the diameter d of each loop being preferably up to about 300 centimeters. The number of turns of wire N, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention.

It is also to be understood that the applied magnetic field which results in a combined magnetic flux density along predetermined axis 54 may be produced by a sinusoidal signal or from a full-wave rectified signal applied to field coils 36, 38. It may also be appropriate in some instances to reduce components of the local magnetic field which are not parallel to predetermined axis 54 to zero through the use of additional coils positioned at right angles to coils 28 and 30 to create an opposite but equal field. It may also be suitable to reduce the local magnetic field component to zero throughout treatment using additional coils or the like.

Figure 4:
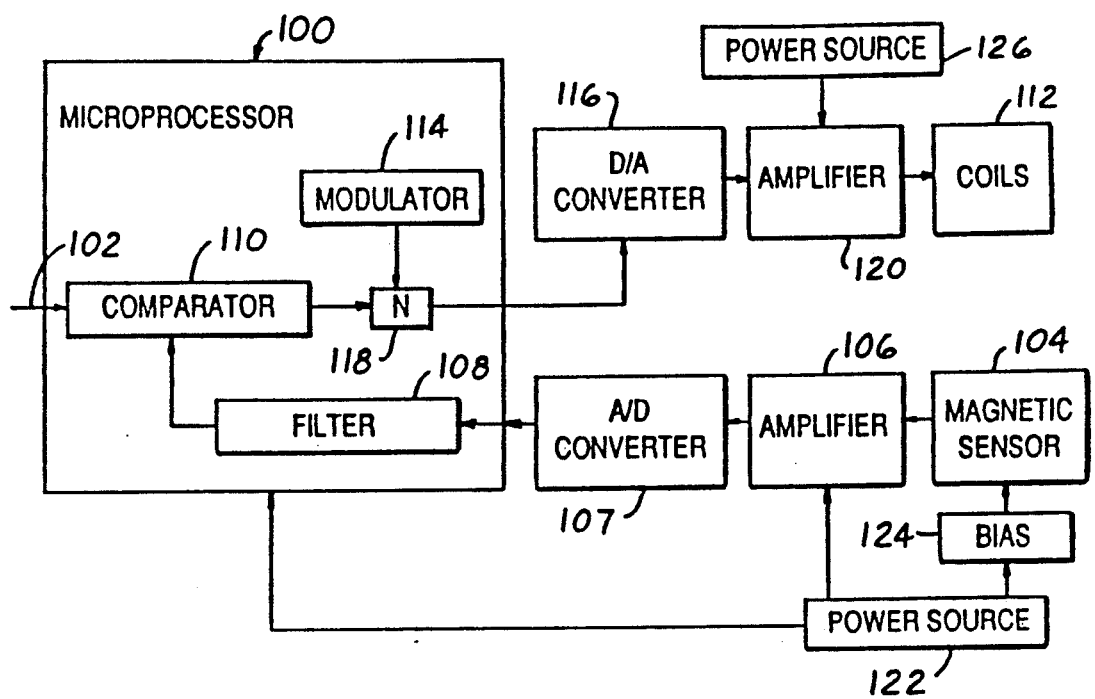
FIG. 4 is a block diagram of the functional elements of a preferred circuit for use in the present invention.

Referring now to FIG. 4 of the drawings, a block diagram is shown which depicts one preferred arrangement of the circuits of cancer treatment apparatus 20 in functional segments. Numerous other circuit arrangements may be possible if the principles of the present invention are faithfully observed. Microcontroller or microprocessor 100 is seen by which the composite magnetic field is maintained at a constant predetermined level despite changes in the ambient component as previously described. In this respect, input 102 is provided by which a set point value of the predetermined composite magnetic flux density along a predetermined axis through the target tissue is input into microprocessor 100. As will be shown, the composite field strength is compared to this set point value to generate an error equal to the difference in the set point value and the measured value of the composite magnetic flux density along the axis.

Magnetic field sensor 104 is provided by which the magnitude of the composite field which passes through the target tissue along the axis is measured. It is preferred that magnetic field sensor 104 comprise a Hall-effect or a flux gate device each of which, as will be known by those skilled in the art, can sense both time-varying and static magnetic fields and each produces an analog signal. The magnetic field sensor 104 constantly monitors the composite magnetic field, sending a signal to microprocessor 100. It will be understood that the output of a Hall-effect or flux gate magnetic sensor is relatively small; thus, magnetic field sensor amplifier 106 is provided by which the signal from magnetic field sensor 104 is amplified, for example, up to three thousand times its original value. Since these devices produce an analog signal, analog-to-digital converter 107 is provided by which the amplified signal from magnetic field sensor 104 is converted to a digital signal which can be used by microprocessor 100. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital converter 107 which is input into microprocessor 100 is filtered by software filter 108 to remove shot noise and sudden fluctuations in the composite field detected by magnetic field sensor 104. Although it is preferred that filter 108 comprise software in microprocessor 100, a discrete filter could be used. In this embodiment, software filter 108 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more. Hence, the time constant of filter 108 should be such that momentary fluctuations are filtered out.

Microprocessor 100 includes logic which calculates the non-zero net average value of the composite magnetic flux density. This non-zero average value is then compared at a comparator 110 in microprocessor 100 to the predetermined dc reference or offset value which is input into microprocessor 100 via input 102. It should be noted that this reference value is preferably established by dedicated circuitry in microprocessor 100, although variable input means could be included by which the set point value could be changed. An error statement is then generated defining the difference in the measured value of the composite magnetic flux density and the set point or reference value. Microprocessor 100 then determines the magnitude of the output necessary to drive magnetic field generating coils 112 to bring the composite magnetic flux density back to the set point.

Software field modulator or oscillator 114 is provided by which an ac or fluctuating component is superimposed on the digital output signal which is input into digital-to-analog converter 116. From the previous discussion of the present invention, it will be understood that software field modulator 114 of microprocessor 100 in the preferred embodiment of the present invention is preset to a fixed, predetermined frequency to produce the desired predetermined ratio of frequency-to-magnetic flux density value. In another embodiment, the feedback system of the present invention is such that changes in the composite magnetic flux density are measured, whereupon microprocessor 100 determines the necessary change in frequency to maintain the predetermined relationship. In that embodiment, software field analog converter 116 be provided on-board the microprocessor chip. Hence, software field modulator 114 provides the ac component at node 118.

The signal from digital-to-analog converter 116 is fed to voltage-to-current amplifier 120, the output of which drives magnetic field generating coils 112 in the desired manner. Hence, the composite field is held substantially constant despite changes in the ambient While several arrangements of power sources are suitable, it is preferred that power supply 122 be provided to power magnetic field sensor amplifier 106, microprocessor 100 and magnetic field sensor 104, the latter via bias circuitry 124. A separate power source 126 is preferred for voltage to current amplifier 120.

Having fully described one preferred embodiment of the apparatus of the present invention, including its manner of construction, operation and use, the method of the present invention will now be described. It is to be understood that this description of the method incorporates the foregoing discussion of the novel apparatus. In one embodiment, the present invention provides a method of reducing the rate of growth of a neoplasm in man or animals. This is achieved in one aspect by generating a fluctuating, directionally-oriented magnetic field which projects through the cancer cells, for example a malignant neoplasm such as a sarcoma, in the presence of a chemotherapeutic agent as previous described. It is to be understood that the present invention may also be useful in reducing the rate of growth of benign tumors. The magnetic field generating means preferred for use is previously described. The magnetic field so generated has a magnetic flux density of precisely controlled parameters which passes through the target neoplasm parallel to a predetermined axis projecting through the neoplasm. As will be known by those skilled in the art and as has been clearly explained, the local magnetic field to which the neoplasm is subjected will have a component which is parallel to the predetermined axis and which thus aids or opposes the applied or generated magnetic field along the axis. At times, the local component may be zero. In the method of the present invention, the density of this combined magnetic flux, and more specifically the net average non-zero value of the combined magnetic flux density, is controlled to provide a precise relationship between the flux density along the axis and the frequency of the applied magnetic field which is oscillating at a predetermined value. Most preferably this is accomplished by adjusting the intensity of the applied field to compensate for changes in the local field. Thus, in one embodiment, the present invention provides a method of treating cancer by creating a magnetic field which penetrates a malignant neoplasm and which has a predetermined relationship between frequency of oscillation and average flux density. In the most preferred embodiment, the predetermined relationship or ratio of frequency-to-field intensity is determined with reference to the equation:ps $$f_c/B = q/(2\pi m)$$

where $f_c$ is the frequency of the combined magnetic field along the predetermined axis in Hertz, B is the non-zero net average value of the magnetic flux density of the combined magnetic field parallel to the axis in Tela and q/m is in Coulombs per kilogram and has a value of from about $5 \times 10^5$ to about $100 \times 10^6$. B preferably has a value not in excess of about $1 \times 10^{-2}$ Tela.

In order to maintain a fluctuating magnetic field having the desired parameters, it may be necessary to monitor changes in the composite magnetic field parallel to the predetermined axis. As stated, this is preferably carried out with a Hall-effect device or the like which is capable of sensing both static and time-varying magnetic flux and which produces an analog signal. This analog signal is periodically sampled by microprocessing means which then calculates the necessary frequency and/or magnitude of the applied magnetic field to maintain the preprogrammed, predetermined ratio previously described. Of course, it will now be understood that it is the combined magnetic flux which is sensed by the magnetic field sensor. The magnetic field generating means is used to adjust the magnitude of this composite field where In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintain the predetermined relationship of the present invention.

Hence, in one aspect the method of the present invention includes the steps of creating and maintaining a predetermined relationship between the frequency of a fluctuating magnetic field and the flux density of the field. In particularly preferred embodiments, a frequency of 16 Hertz and an average flux density of $2.09 \times 10^{-5}$ Tesla are utilized which corresponds to cyclotron resonance for $Ca^{++}$. This combination of frequency and flux density is particularly useful in decreasing the proliferation rate of cancer cells in the presence of a chemotherapeutic agent. Another preferred frequency which is useful is 16 Hertz and $4.07 \times 10^{-5}$ Tesla which corresponds to cyclotron resonance for $K^+$.

In a preferred embodiment of the method of the present invention, the ratio of frequency-to-flux density is determined by selecting a preselected ion present in the neoplasm and tuning the fluctuating composite magnetic flux density to the specific cyclotron resonance frequency for the ion. The preferred ions for increasing the inhibition of cancer cells in the presence of a chemotherapeutic agent are $Li^+$, $K^+$, $Mg^{++}$, and $Ca^{++}$. Tuning to other ions such as $Mn^{++}$, $Zn^{++}$ or $Cu^+$ may also provide beneficial results.

Finally, the subject neoplastic tissue is exposed to the therapeutic magnetic flux in accordance with the present invention for a period of time sufficient to bring about the desired result. It is believed that exposure in accordance with the present invention of approximately 0.5 hr. to 24 hr./day will typically provide beneficial results.

In another preferred embodiment of the present invention, the treatment heads of cancer treatment apparatus 20 contain two discrete but otherwise equal windings. Each head contains a dc winding and an ac winding. These windings are closely wound, either as alternate wires, as alternate layers, or in adjacent planes. Those skilled in the art will recognize that the closeness of the winding arrangement will ensure that the two separate magnetic fields generated at a point distant from the two windings (when each carries substantially the same current) will be substantially the same. The dc winding in one coil is connected in series aiding to the dc winding in the other coil. The ac winding in one coil is similarly connected in series aiding to the ac winding in the other coil.

The pair of dc windings are energized by a dc power supply that provides a current which reduces the component of the local or ambient field along the axis of the coil pair at the desired treatment region to a value that is substantially zero. Again, the ambient field is measured by magnetic field sensing means such as a Hall device or a fluxgate magnetometer or the like. The ac windings, in this embodiment, are preferably energized by a full-wave rectifier circuit providing a current which produces a resulting ac magnetic field component along the coil axis at the desired treatment region that varies in time at the therapeutic frequency. The rms current of the rectified signal in the ac coil pair is adjusted until a preselected rms magnetic field component at the treatment region is achieved. It will be understood that once the ambient field is measured, knowledge of the coil geometry and number of turns will allow a predetermined calibration, enabling the operator to automatically achieve the required ambient field nulling current as well as the rms current necessary to create the preselected rms magnetic field.

In this embodiment utilizing a rectified signal in the ac windings, the frequency of the fluctuating magnetic field is set at a predetermined value, and the effective or root-mean-square value of the applied magnetic flux density is then regulated to produce a ratio of frequency to flux density that acts to reduce the rate of growth of cancer cells. Preferred ratios of frequency-to-field intensity are determined with reference to the equation:

$$\frac{f_0}{B_0} = q/2\pi m$$

where $f_0$ is the frequency of the fluctuating magnetic field in Hertz, $B_0$ is the non-zero rms value of the magnetic field component winding along the coil axis in Tesla, $(q/m)$ is in Coulombs per kilogram and has a value of from about $5 \times 10^5$ to about $100 \times 10^6$. $B_0$ preferably has a value not in excess of $1 \times 10^{-2}$ Tesla. In one embodiment, the values of q and m are selected with reference to the charge and mass of a preselected ion. Other relationships between frequency and magnitude may be useful or even desirable in a particular application.

In another embodiment, a sinusoidal current is employed in the ac windings with a direct current offset resulting in a non-zero average magnetic field to achieve the required magnetic field along the predetermined axis that is therapeutically effective.

Figure 5:
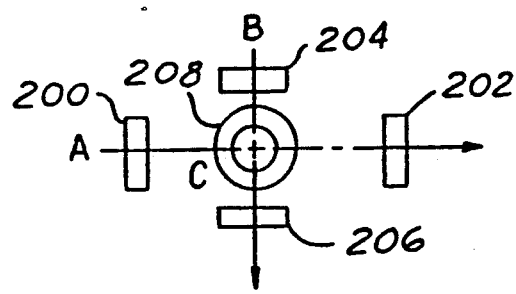
FIG. 5 is a side elevational view in which the present invention is shown utilizing three pairs of coils.

In still another embodiment, and referring now to FIG. 5 of the drawings, three pairs of Helmholtz-like coils generate applied magnetic fields along the x, y and z axes of a Cartesian coordinate system. Coil pair A comprises treatment heads 200 and 202. Coil pair B comprises treatment heads 204 and 206, and coil pair C similarly comprises a pair of opposed coils, only one of which is shown in phantom as treatment head 208. It will be appreciated that these coils may comprise single windings or may be provided in the combination ac and dc windings as previously described. Also, it is preferred that each pair be provided with a magnetic field sensing device in order to measure the magnetic field component along each respective axis. In other words, the axes of the three coil pairs will be mutually perpendicular, intersecting at the desired treatment region, i.e., the target malignant neoplasm. The therapeutic frequency is generated by each coil pair in the aforementioned described manner. Where the coil pairs include ac and dc windings, the ambient field component along each axis is reduced to substantially zero.

In still another embodiment of the present invention, the growth rate of a neoplasm in the presence of a chemotherapeutic agent is reduced by creating and maintaining a predetermined relationship between the frequency of the fluctuations and the non-zero average value of the magnetic flux density along the predetermined axis based on the charge-to-mass ratio of the preselected ion, wherein this predetermined relationship is determined using the equation $f_{ch} = XBq/2\pi m$. Accordingly, $f_{ch}$ is the frequency of the fluctuating magnetic flux density in Hertz, B is the non-zero average value of the flux density parallel to the predetermined axis in Tesla, q is the charge of the preselected ion in Coulombs, m is the mass of the preselected ion in kilograms, and X is a preselected odd integer greater than one. In this manner, a number of higher harmonic frequencies are provided by which therapeutic results may be achieved.

It will be recognized that the fundamental therapeutic frequency $f_c$ is effectively multiplied by a selected odd integer to produce a frequency which also causes the desired therapeutic result. Unless otherwise specified, as used herein, the term "odd integers" or "odd integer" shall mean positive, non-zero integers. The preferred odd integers for use in the present invention which provide harmonic frequencies that should be effective in reducing the growth rate of cancer are selected from the group consisting of the following integers: three, five, seven, nine, eleven, thirteen, fifteen, seventeen and nineteen. Additional harmonic frequencies based on multiplying the fundamental frequency by an odd integer may also be suitable in some applications. As indicated, the frequencies for a given preselected ion and known magnetic flux density B can be determined with reference to the equation $f_{ch}=XBq/2\pi m$ where $f_{ch}$ is the frequency in Hertz of the fluctuating magnetic field along a predetermined axis extending through the target tissue, B is the magnetic flux density along the axis in Tesla, q is the charge of the preselected ion in Coulombs, m is the mass of the preselected ion in kilograms, and X is a selected odd integer greater than one. It is believed that many of the preferred odd multiple harmonic frequencies will be substantially as effective in treating cancer as are the fundamental frequencies. A more thorough description of harmonic tuning is set forth in the aforementioned U.S. patent application Ser. No. 343,017 which is incorporated herein by reference.

In still another aspect, the present invention provides a method for decreasing the proliferation rate of cancer cells which comprises generating an applied magnetic field parallel to a predetermined axis which projects through the designated space. In the presence of at least two different predetermined ionic species in the target cancer cells or tissue and a chemotherapeutic agent, the neoplasm is exposed to the applied magnetic field. In one embodiment, the neoplasm is also exposed to a local magnetic field having a component parallel to the predetermined axis. The magnetic flux density along the predetermined axis is fluctuated to create a non-zero average value. Where a local field is also present, this non-zero average value is the net non-zero average value of the applied and local field components parallel to the predetermined axis as previously described in connection with the other embodiments of the present invention.

A predetermined relationship between the frequency of the fluctuations and the non-zero average value of the magnetic flux density along the axis is then created and maintained which simultaneously controls the movement of two or more preselected ions. Ion movement is brought about to decrease the growth rate of the neoplasm. In one embodiment, the predetermined relationship is determined by first solving the equation $f_c=Bq/2\pi m$ at a generally randomly selected value of B for each distinct preselected ion, where $f_c$ is the frequency of the field fluctuations in Hertz, B is the non-zero average value of the flux density parallel to the predetermined axis in Tesla, q is the charge of each preselected ion in Coulombs, and m is the mass of each preselected ion in kilograms. The value of B is preferably less than about $10^{-2}$ T. This establishes the fundamental cyclotron frequency for each ion. A value $f_{cs}$ is preferably selected such that none of the individual ion $f_c$ values deviate more than 5 percent from the $f_{cs}$ value. In most instances, there will be no $f_{cs}$ value available based on the fundamental $f_c$ values of the preselected ions. Accordingly, a higher odd harmonic frequency of at least one of the preselected ions is determined with the equation $f_{ch}=XBq/2\pi m$ as previously explained. The values of $f_c$ and $f_{ch}$ are examined to determine whether an $f_{ch}$ value can be selected based on a 10 percent and most preferably a 5 percent deviation factor. If not, the process is continued for each value of $f_{ch}$, beginning with the lowest odd harmonic $f_{ch}$ values until a value of $f_{cs}$ can be established within the 5 percent deviation. Hence, at the value selected for B during the calculation of the $f_c$ or $f_{ch}$ values, the magnetic flux density to which the target tissue is exposed is fluctuated along the axis at the $f_{cs}$ frequency. This specific relationship between frequency and field strength brings about simultaneous transmembrane movement of the preselected ions for decreasing the proliferation rate of the target cancer cells.

In more detail, the fundamental frequency at which the fluctuating magnetic field would be oscillated for cyclotron resonance regulation of transmembrane ion movement is calculated individually for each different ionic species to be regulated using the equation $f_c=Bq/2\pi m$ for a selected value of B, which is again the non-zero average value of the flux density along the predetermined axis. As previously explained, $f_c$ is in Hertz, q is in Coulombs, m is in kilograms, and q/m is the charge-to-mass ratio of the preselected ion. Once the fundamental cyclotron resonance frequency ($f_c$) of each ion to be regulated is calculated, a regulating frequency ($f_{cs}$) is determined which is preferably within 5 percent of the fundamental frequency $f_c$ or an odd harmonic frequency $f_{ch}$ of each preselected ion. The odd harmonic frequencies are determined again using the equation $f_{ch}=XBq/2\pi m$, where X is an odd integer greater than one. It will be understood that the equation $f_{ch}=XBq/2\pi m$ can be used to determine the fundamental frequency $f_c$ by using a value of 1 for X. While the value of $f_{cs}$ will not typically be available which is common to the fundamental frequencies and/or odd harmonic frequencies for each preselected ion, it has been found that an $f_{cs}$ value which is within about 10 percent and preferably about 5 percent of each $f_c$ value or $f_{ch}$ value of the ions to be regulated satisfactorily provides simultaneous transmembrane movement of each preselected ion in the field.

It will also be understood that the values of $f_{ch}$ are a function of B. Thus, it may be possible to obtain an $f_{cs}$ value for a particular set of ions which is within the preferred 5 percent deviation at a designated B value, but not a higher B value. For use in the present invention, the value of B is preferably less than about $1\times10^{-2}$ T, with a peak-to-peak amplitude of about 2.0 to about 20,000$\mu$ Tesla. The preferred ions are those previously set forth. A more thorough description of multiple tuning is set forth in the aforementioned U.S. patent application Ser. No. 343,017 which is incorporated herein by reference.

It will therefore be appreciated that in the broadest sense, the present invention provides a method and apparatus for regulating the growth characteristics of cancer cells, i.e. treating cancer, by subjecting the cells to a magnetic environment in which the ratio of the magnetic flux density to the frequency of oscillation of a fluctuating field component is maintained at a predetermined relationship based on the cyclotron resonance frequency of at least one ion in the field. This relationship may be selected to decrease the proliferation rate of cancer cells exposed to a particular chemotherapeutic agent or selected to increase the differentiation of cancer cell neurites to inhibit malignancy. It may be possible to select a relationship which decreases the rate at which cancer cell proliferation occurs even without the use of a chemotherapeutic agent. In its most preferred embodiments, the present invention provides a method and apparatus which includes tuning to the cyclotron resonant frequency of $Ca^{++}$ or $K^+$ or a selected multiple of these frequencies in the presence of a chemotherapeutic agent to decrease proliferation rate. In another most preferred aspect, the predetermined relationship is based on multiple harmonic tuning for both $Ca^{++}$ and $Mg^{++}$ in the presence of a chemotherapeutic agent where the relationship represents three times the fundamental frequency of the calcium ion and five times the fundamental frequency of the magnesium ion. In the latter case, it is the formation of neurites which is stimulated.

Figure 6:
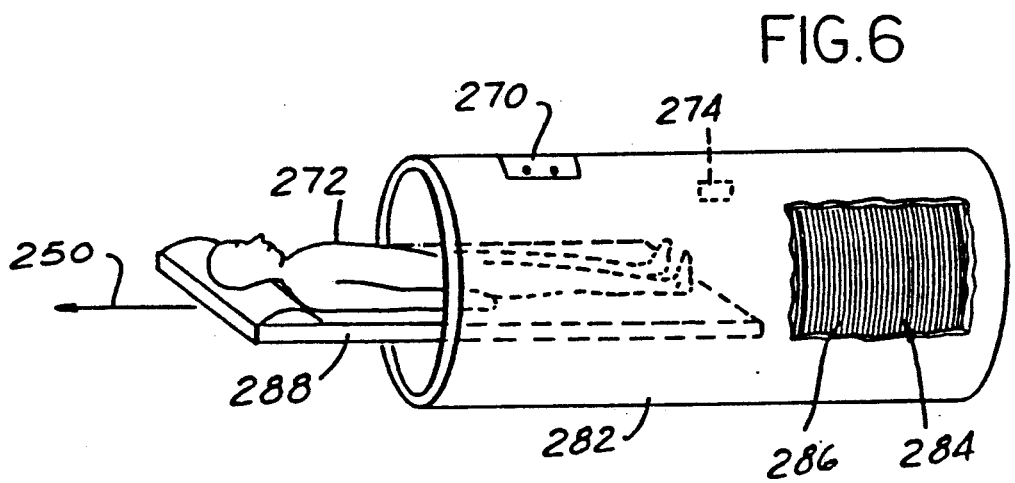
FIG. 6 is a perspective view of the present invention for use in systemic treatment of cancer.

In still another aspect the present invention provides an apparatus for the systemic therapeutic treatment of cancer. By "systemic treatment" it is meant that substantially all of the subject's body is simultaneously exposed to the therapeutic magnetic fields in accordance with the present invention. Accordingly, and referring now to FIG. 6 of the drawings, systemic treatment apparatus 280 is shown which comprises a tube or cylinder 282 of a non-magnetic material such as plastic. Tube 282 houses a large solenoid 284 which contains multiple turns of wire 286 and which extends substantially the entire length of systemic treatment apparatus 280. Gurney or platform 288 is provided on a track system (not shown) which allows platform 288 to move between a first position outside of tube 282 to a second position inside of tube 282. A controller 270 is provided along with the necessary circuitry for energizing solenoid 284 to create a magnetic field in the direction of axis 250, which in this embodiment projects through the central bore of solenoid 284. In other words, and as will be appreciated by those skilled in the art, the magnetic flux generated by solenoid 284 will run through the center of the coil. Patient 272 is placed on a platform 288 and platform 288 is then moved into position inside tube 282. Thus patient 272 is positioned inside solenoid 284 with the applied magnetic flux penetrating the patient's entire body in the direction of predetermined axis 250. In one embodiment a magnetic field sensor 274 is also provided to measure the magnetic flux density along axis 250 and may be mounted on a track system within tube 282. It may be suitable in some applications to mount tube 282 on a rotatable stand such that tube 282 can be rotated to change the position of patient 272 and axis 250 with respect to the local magnetic field. Other configurations of systemic treatment apparatus 280 may be suitable or even desirable in a particular application such as large flat coils (for example having diameters of six feet or greater) in Helmholtz arrangement with one coil being placed on each side of patient 272. In this alternative arrangement, axis 250 would extend transverse to the patient's body rather than from toe-to-head as shown in FIG. 6. Of course, the direction of the magnetic field may also be directly opposite to the direction of axis 250 depending upon the direction of current through solenoid 284. Systemic treatment apparatus 280 is thus used to create a magnetic field of predetermined parameters inside tube 282. While this predetermined relationship is preferably maintained by adjusting the applied flux to compensate for changes in the local field component; alternatively, the frequency can be adjusted to preserve the desired ratio.

For systemic treatment, a patient 272 afflicted with cancer is placed on platform 288 which is then moved into position within tube 282 and thus within solenoid 284. Patient 272 is then subjected to a fluctuating magnetic flux of the nature previously described for a period of time sufficient to bring about the desired systemic treatment. It is believed that exposure in accordance with the systemic treatment embodiment of the present invention of about 0.5 hr. to 24 hr./day until the desired result is achieved.

Figure 7:
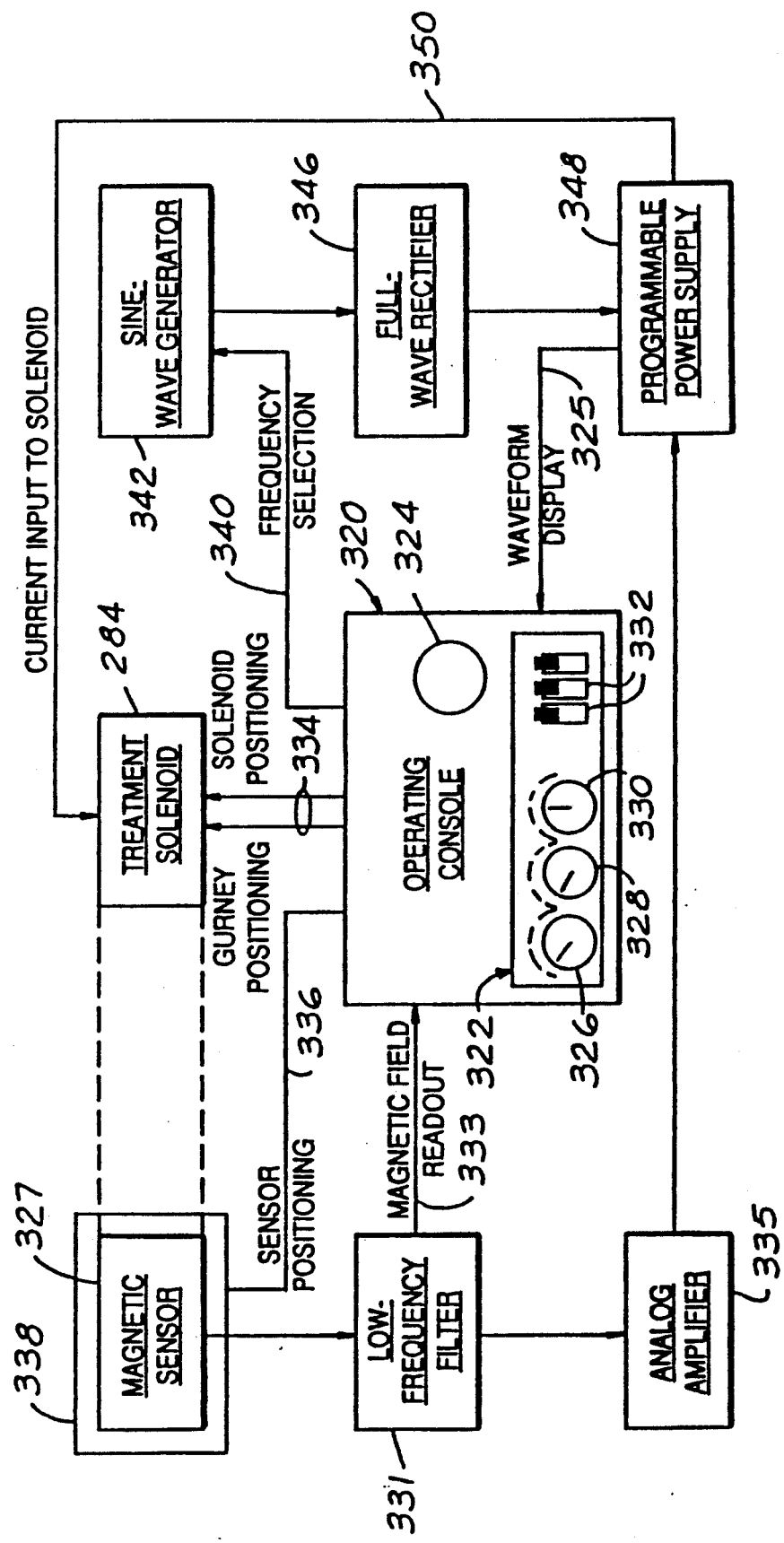
FIG. 7 is a block diagram of the circuitry of one embodiment of the present invention for use in systemic treatment.

Referring now to FIG. 7, a block diagram is shown which is preferred for use in connection with the systemic treatment apparatus 280. Operating console 320 forms the control center for operating systemic treatment apparatus 280. The console is comprised of a plurality of control elements 322 and a visual display device 324 for monitoring the wave form display of the solenoid current signal 325. The plurality of control elements 322 include a gurney positioning dial 326 for controlling the lateral movement of the gurney platform. Magnetic field sensor adjusting dial 328 allows the operator to selectively position the magnetic field sensor 327 within the center of treatment solenoid 284. The treatment structure rotating dial 330 allows the operator to rotate the concentric solenoid and platform 288 in the horizontal plane in that embodiment where a supporting stand or turntable (not shown) is provided. This horizontal movement allows the solenoid coil to be positioned so that it may compensate for undesired local magnetic fields. Switch elements 332 allow the operator to effect various other control tasks, such as turning the concentric solenoid current on or off, or setting the cyclotron resonance frequency for the ion of choice. Each of the above-mentioned dials and switch elements produce signals which go to various elements of system treatment apparatus 280 to accomplish the various functions described herein. The signal produced by the gurney positioning dial 326 leaves operating console 320 along cable 334 as does the signal produced by the treatment structure rotating dial 330. The signals 334 interface with various motors and other drive hardware to effect the positioning of platform 288 within solenoid 284 and the positioning of tube 282 with respect to the local magnetic field. Control line 336 transmits the signal developed by the magnetic field sensor adjusting dial 328 to a magnetic sensor positioning device 338 which allows the magnetic sensor 327 to be positioned at various locations within the center of the solenoid 284. After dials 326 through 330 and switches 332 have been set, systemic treatment apparatus 280 is ready for operation. The frequency which has been selected by the operator is output along line 340 to the sine wave generator 342. The sine wave generator 342 responds to the frequency selected in accordance with the principles of the present invention by generating a sinusoidal waveform which possesses one-half of the desired frequency with no DC offset. The signal is then sent from the sine wave generator 342 to a full-wave rectifier circuit 346. Rectifier 346 not only transforms the sinusoidal waveform produced by generator 342 to a rectified DC signal, it also has the effect of doubling the frequency of the output of the sine wave generator. The rectified signal is then sent from the full-wave rectifier 346 to the programmable power supply 348 where it is amplified to a sufficient power level which is necessary to develop a sufficiently strong magnetic field within the solenoid 284. The amplified signal is then sent from the programmable power supply 348 along cable 350 to solenoid 284. Solenoid 284 then converts the amplified current to a uniform magnetic field density within the concentric solenoid winding 284 along axis 250 shown in FIG. 6. Because of localized magnetic fields, the magnetic field, as it exists within the concentric solenoid winding, is not always absolutely predictable. Thus, magnetic sensor 327 is mounted in close proximity to the patient so that the magnetic flux density within solenoid 284 can be constantly monitored. A signal, which is proportional to the magnetic flux density within treatment solenoid 284, is output by the magnetic sensor 327 and then filtered by filter 331 to eliminate any undesired high-frequency elements. The output of low-frequency filter 331 is then delivered to operating console 320 along cable 333 so that it can be displayed on the visual display device 324. The output of low-frequency filter 331 is also sent to analog amplifier 335 so that it can be properly conditioned to be used within the programmable power supply 348. The programmable power supply 348 uses the output from analog amplifier 335 as a means for maintaining a uniform density magnetic field within the center of solenoid 284. This task may be performed within the programmable power supply by means of standard analog feedback techniques or may be accomplished by means of a digital processor.

The following examples are provided to more fully illustrate the present invention and are not intended to limit the scope of the invention as defined in the appended claims.

EXAMPLE I

N-18 neuroblastoma tumor cells from the American Type Culture Collection (ATCC) were cultured in Linbro 12-well culture plates in either I-10 or I-H media, at 37° C., with 5% $CO_2$ in air at 100% humidity. The formulae for the media is as follows:

| I-10 | |
|---|---|
| Dulbecco's Minimum Essential Medium (double strength) | 50 ml |
| Fetal Calf Serum | 10 ml |
| 20% Glucose solution | 3 ml |
| L-Glutamine (200 mM solution) | 1 ml |
| Penicillin/Streptomycin (Gibco Prepared) | 1 ml |
| $H_2O$ | q.s. 100 ml |
| I-H | |
| DMEM (2X) | 50 ml |
| Horse Serum | 25 ml |
| 20% Glucose | 3 ml |
| L-Glutamine | 1 ml |
| Penicillin/Streptomycin (Gibco Prepared) | 1 ml |
| $H_2O$ | q.s. 100 ml |

50% of the cultures received ARA-C (Cytosine Arabinoside) at a final concentration of 0.25 micrograms/ml, an inhibitor of neuroblastoma growth. Experimental cultures also received 24 hour combined magnetic field stimulation adjusted to ion cyclotron resonance values for $Ca^{++}$ or $K^+$ according to the method and formula of the present invention. Treatment was accomplished by placing the culture dishes in the space between the energized Helmholtz-aiding coils in the incubator so that the combined magnetic fields passed through the culture medium and cells parallel to the surface of the medium and the bottom of the dish. The following protocol was used:

| Culture | ARA-C | CR Ion | No. of Cultures |
|---|---|---|---|
| Control I-10 | Yes | none | 9 |
| Control I-H | Yes | none | 9 |
| Control I-10 | No | none | 9 |
| Control I-H | No | none | 9 |
| I-10 | Yes | Ca | 9 |
| I-10 | No | Ca | 9 |
| I-H | Yes | Ca | 9 |
| I-H | No | Ca | 9 |
| I-10 | Yes | K | 9 |
| I-10 | No | K | 9 |
| I-H | Yes | K | 9 |
| I-H | No | K | 9 |

The medium is each culture dish was renewed every other day. After 3 days of culture, the dishes were removed from the incubator, and the cell proliferation rate was established by making cell counts in each dish. The cells having recognizable neurites (outgrowths at least twice as long as the cell diameter) were also counted. The data are expressed as number of cells per dish and percent of cells having neurites.

| | RESULTS | | | |
|---|---|---|---|---|
| Category | No. Cells/Dish | p vs C | % Neurites | p vs C |
| C + ARA-C (I-10) | 37.50 | — | 16.87 | — |
| C + ARA-C (I-H) | 15.78 | — | 9.29 | — |
| C NO ARA-C (I-10) | 66.78 | — | 12.71 | — |
| C NO ARA-C (I-H) | 46.67 | — | 20.64 | — |
| Ca + ARA-C (I-10) | 46.34 | .10 | 9.92 | .05 |
| Ca + ARA-C (I-H) | 30.78 | .01 | 14.45 | .10 |
| Ca NO ARA-C (I-10) | 64.72 | N.S. | 11.59 | N.S. |
| Ca NO ARA-C (I-H) | 33.33 | .10 | 22.08 | N.S. |
| K + ARA-C (I-10) | 46.56 | .10 | 12.44 | N.S. |
| K + ARA-C (I-H) | 20.44 | N.S. | 12.75 | N.S. |
| K No ARA-C (I-10) | 68.00 | N.S. | 12.57 | N.S. |
| K No ARA-C (I-H) | 24.00 | .01 | 20.93 | N.S. |

These results indicate that CR fields can influence the growth of tumors in vitro and can alter the effects of an antitumor drug on the cells. The tuning for $Ca^{++}$ and $K^+$ had little effect on the outgrowth of neurites. The tuning for Ca had some effect, depressing outgrowth strongly in I-10, which contains strong fetal growth factors and enhancing growth slightly in I-H, which lacks the growth factors of I-10.

Neither $Ca^{++}$ nor $K^+$ tuning overcome the strong effect of cell proliferation factors contained in I-10 medium as a result of the incorporation of the fetal calf serum. The effect was essentially null, even in the presence of ARA-C. However, when I-H was used, which is more nearly similar to normal adult serum by virtue of the absence of the fetal cell proliferation factors, the CR tuning for Ca produced an increase in cell proliferation, partly overcoming the inhibitory effect of the ARA-C.

When $K^+$ tuning was used in I-H medium, in the presence of ARA-C, there was essentially no effect, the ARA-C being a strong inhibitor notwithstanding.

In the absence of the ARA-C, using the I-H medium, Calcium tuning produced a slight depression of cell proliferation.

When K tuning was used in the absence of ARA-C in I-H medium, there was a very strong suppression of cell proliferation. In fact, the suppression produced by the $K^+$ signal was statistically equivalent to the effect of the potent pharmacological agent, suggesting that under some circumstances, the use of cyclotron resonance may be as effective a treatment modality as a standard pharmacological agent, but perhaps without the negative side effects of the pharmacological agent.

EXAMPLE II

In this example the medium was identical to I-10 above, except the serum concentration was reduced to 2.0 ml. In the following table, the reduction in proliferation achieved by the present invention is again demonstrated with respect to the synergistic effect of cyclotron resonance treatment in the presence of chemotherapeutic cancer agents. The experiments were conducted for 72-hour periods. The cells were N-18 neuroblastoma cells.

```
K  = potassium ion (K+)
Ca = calcium ion (Ca++)
H  = Mg/Ca 3/5 harmonic tuning
C− = control plates without ARA-C and without cyclotron resonance exposure
C+ = control plates with ARA-C and without cyclotron resonance exposure
E− = experimental plates without ARA-C and with cyclotron resonance exposure
E+ = experimental plates with ARA-C and with cyclotron resonance exposure
.5 = ½ hour field exposure per 24 hours
24 = continuous field exposure
     (ARA-C = cytosine arabinoside [conc. 0.25 micrograms/ml])
     (cell processes refers to neurites)
```

| ION/TIME | | C− | C+ | E− | E+ |
|---|---|---|---|---|---|
| | | TOTAL CELLS/MM$^2$ +− S.D. | | | |
| K/.5  | H | 47.8−27.4   | 28.5−14.9  | 215.1−124.2 | 43.6−22.9 |
| K/24  | H | 81.9−59.0   | 34.1−19.3  | 218.7−95.8  | 50.3−28.0 |
| Ca/.5 | H | 33.3−15.0   | 18.6−9.0   | 129.3−44.2  | 26.2−17.2 |
| H/.5  | H | 142.9−55.1  | 33.3−22.0  | 167.0−60.4  | 26.3−11.1 |
| Mg/.5 | H | 36.5−40.5   | 11.7−9.8   | 51.7−34.8   | 10.7−7.8 |
| (H = Mg/Ca. 3/5 Harmonic Tuning) | | | | | |
| | | % CELLS WITH PROCESSES +− S.D. | | | |
| K/.5  | H | 10.8−6.3    | 13.8−8.9   | 11.1−6.8    | 10.0−7.5 |
| K/24  | H | 9.0−4.6     | 7.2−7.6    | 7.3−3.2     | 4.2−3.7 |
| Ca/.5 | H | 12.9−6.8    | 19.4−11.9  | 17.2−6.3    | 14.6−10.9 |
| H/.5  | H | 21.2−6.6    | 12.9−8.7   | 20.1−5.9    | 15.2−7.6 |
| Mg/.5 | H | 9.9−6.9     | 6.3−11.2   | 8.6−5.2     | 3.8−7.7 |

| ION/TIME | | C− vs C+ | E− vs E+ | C− vs E− | C+ vs E+ |
|---|---|---|---|---|---|
| | | STATISTICAL COMPARISONS, TOTAL CELLS (t, (p)) | | | |
| K/.5  | H | 3.67 (<.001)  | 8.03 (<.001)  | 7.89 (<.001)  | 3.35 (<.005) |
| K/24  | H | 4.56 (<.001)  | 9.98 (<.001)  | 7.29 (<.001)  | 2.85 (<.01) |
| Ca/.5 | H | 5.08 (<.001)  | 13.06 (<.001) | 12.35 (<.001) | 2.36 (<.05) |
| H/.5  | H | 11.09 (<.001) | 13.75 (<.001) | 1.78 (N.S.)   | 1.72 (N.S.) |
| Mg/.5 | H | 3.56 (<.005)  | 6.99 (<.001)  | 1.72 (N.S.)   | 0.54 (N.S.) |
| | | % CELLS WITH PROCESSES (t, (p)) | | | |
| K/.5  | H | 1.63 (N.S.)   | 0.65 (N.S.)   | 0.19 (N.S.)   | 1.96 (=.05) |
| K/24  | H | 1.20 (N.S.)   | 3.75 (<.001)  | 1.88 (N.S.)   | 2.11 (<.05) |
| Ca/.5 | H | 2.86 (<.01)   | 1.26 (N.S.)   | 2.81 (<.01)   | 1.80 (N.S.) |
| H/.5  | H | 4.56 (<.001)  | 3.05 (<.01)   | 0.77 (N.S.)   | 1.18 (N.S.) |
| Mg/.5 | H | 1.04 (N.S.)   | 3.09 (<.005)  | 0.43 (N.S.)   | 1.04 (N.S.) | n for all experiments = 36

Thus, it is apparent that there has been provided in accordance with the invention a method and apparatus that fully satisfies the objects, aims and advantages set forth above. While the invention has been described in connection with specific embodiments thereof, it is evident that many alternatives, modifications, and variations will be apparent to those skilled in the art in light of the foregoing description. For example, it is to be understood that higher harmonic tuning and multiple ion tuning as described herein may be useful in connection with the contemporaneous use of chemotherapeutic cancer agents. Accordingly, it is intended to embrace all such alternatives, modifications and variations that fall within the spirit and broad scope of the appended claims.

What is claimed is:

1. A method for treating cancer comprising the steps of:
   positioning a magnetic field generating means adjacent a biological subject afflicted with cancer in an existing ambient magnetic field;
   generating an applied magnetic field with said magnetic field generating means, said applied magnetic field extending along an axis through said subject and combining with said ambient magnetic field along said axis to form a composite magnetic field;
   measuring the magnitude of said ambient magnetic field and said applied magnetic field along said axis;
   fluctuating said applied magnetic field and controlling the magnitude of said applied magnetic field along said axis to create a ratio between the frequency of said fluctuations of said applied magnetic field and the magnitude of said composite magnetic field which regulates the growth characteristics of cancer cells in said subject; and
   regulating said frequency of said fluctuations based on said measured ambient magnetic field and the magnitude of said applied magnetic field to maintain said ratio as the magnitude of said applied magnetic field changes along said axis.

2. The method recited in claim 1, wherein said ratio of said frequency to said magnitude of said composite magnetic field is determined by using the equation $$f_c/B = q/(2\pi m)$$

where $f_c$ is said frequency in Hertz, B is the average value of said composite magnetic field in Tesla along said axis, q/m has a value of from about $5 \times 10^5$ to about $100 \times 10^6$ in Coulombs per kilogram and where B preferably has a value not in excess of about $1 \times 10^{-2}$ Tesla.

3. The method recited in claim 2, wherein q and m are, respectively, equal to the charge and mass of a preselected ionic species.

4. The method recited in claim 3, wherein said preselected ionic species is selected from the group consisting of $Zn^{++}$, $Mn^{++}$, $Cu^+$, $Li^+$, $K^+$, $Mg^{++}$ and $Ca^{++}$.

5. The method recited in claim 1 wherein a chemotherapeutic cancer agent is substantially contemporaneously present in said subject during said treatment.

* * * * *